United States Patent
Bao et al.

(10) Patent No.: US 11,007,047 B2
(45) Date of Patent: May 18, 2021

(54) ENDOLEAK PREVENTING STENT GRAFT SYSTEM

(71) Applicant: THE SECOND MILITARY MEDICAL UNIVERSITY, Shanghai (CN)

(72) Inventors: Junmin Bao, Shanghai (CN); Jian Dong, Shanghai (CN); Liangxi Yuan, Shanghai (CN); Yanchun Meng, Shanghai (CN); Jian Zhou, Shanghai (CN); Zaiping Jing, Shanghai (CN)

(73) Assignee: THE SECOND MILITARY MEDICAL UNIVERSITY, Shanghai (CN)

( * ) Notice: Subject to any disclaimer, the term of this patent is extended or adjusted under 35 U.S.C. 154(b) by 792 days.

(21) Appl. No.: 15/537,429

(22) PCT Filed: Dec. 18, 2015

(86) PCT No.: PCT/CN2015/097972
§ 371 (c)(1),
(2) Date: Jun. 14, 2018

(87) PCT Pub. No.: WO2016/095864
PCT Pub. Date: Jun. 23, 2016

(65) Prior Publication Data
US 2019/0167411 A1   Jun. 6, 2019

(30) Foreign Application Priority Data
Dec. 19, 2014   (CN) .......................... 201410817578.6

(51) Int. Cl.
*A61F 2/07* (2013.01)
*A61L 31/10* (2006.01)
(Continued)

(52) U.S. Cl.
CPC .............. *A61F 2/07* (2013.01); *A61L 31/022* (2013.01); *A61L 31/06* (2013.01); *A61L 31/10* (2013.01);
(Continued)

(58) Field of Classification Search
CPC .. A61F 2/07–2002/077; A61F 2550/0067–007
See application file for complete search history.

(56) References Cited

U.S. PATENT DOCUMENTS

| | | |
|---|---|---|
| 2003/0176911 A1 | 9/2003 | Iancea |
| 2006/0095124 A1 | 5/2006 | Benz |

(Continued)

FOREIGN PATENT DOCUMENTS

| | | |
|---|---|---|
| CN | 1403170 A | 3/2003 |
| CN | 102088927 A | 6/2011 |

OTHER PUBLICATIONS

"Mesh", Dictionary.com, 5 pages, accessed Jul. 16, 2020. (Year: 2020).*

*Primary Examiner* — Rebecca S Preston
(74) *Attorney, Agent, or Firm* — Opes IP Consulting Co., Ltd.

(57) ABSTRACT

An endoleak preventing stent graft system, used for preventing the endoleaks except for type II endoleak, comprising: a metal mesh support layer fit for the shape of the artery blood vessel; a cover film layer covering on said metal mesh support layer; and a flexible mesh layer covering outside said cover film layer, said flexible mesh layer fills up the gap formed between said cover film layer and the inwall of said artery blood vessel under the effect of the flexibility of itself.

2 Claims, 8 Drawing Sheets

(51) Int. Cl.
*A61L 31/02* (2006.01)
*A61L 31/06* (2006.01)
*A61L 31/14* (2006.01)
*A61L 33/18* (2006.01)

(52) U.S. Cl.
CPC ............ *A61L 31/146* (2013.01); *A61L 33/18* (2013.01); *A61F 2002/077* (2013.01); *A61F 2210/0076* (2013.01); *A61F 2230/0089* (2013.01); *A61F 2230/0091* (2013.01); *A61L 2400/04* (2013.01)

(56) References Cited

U.S. PATENT DOCUMENTS

2007/0239265 A1* 10/2007 Birdsall ................ A61F 2/2412
623/1.26
2016/0081826 A1* 3/2016 Fredrickson ............ C08L 75/04
623/23.7

* cited by examiner

ENDOLEAK PREVENTING STENT GRAFT SYSTEM

FIELD OF THE INVENTION

The present invention belongs to medical devices area, and relates to a type I endoleak preventing stent graft system with a sponge structure optimized on circumferential stress.

BACKGROUND OF THE INVENTION

The arterial aneurysm is one of the most common disabling and lethal diseases, and may occur in any artery of human body, especially in the elderly. The arterial aneurysm could appear as many sizes, shapes and positions. The Ad Hoc Committee on Reporting Standards of the Society for Vascular Survey defines the arterial aneurysm as a permanent and limited enlargement of the aorta to greater than 1.5 times diameter of the normal aorta, so as to standardize and classify in clinical decision making.

Compared to the traditional open operation, the endovascular graft exclusion treatment using a covered stent for the arterial aneurysm and the aortic dissection has advantages that less wound, fast recovery and short hospital stays. However, a specific complication, endoleak, cannot be avoided completely so far. The endoleak is one of the most important complications of the endovascular graft exclusion, and has an occurrence rate of 45%. The endoleak can be divided into type I to type V, and the following describes the type I endoleak which relates to the present invention.

Type I endoleak is caused by the bad fit between the stent film and the landing zone of the blood vessel inwall, which further leads to a blood leak to the aneurysm cavity from the proximal end or the distal end of the covered stent. Type I endoleak has an occurrence rate of about 10%, and can be found by an angiography during operation. The type I endoleak may cause a high pressure in the aneurysm cavity or a continuous enlargement which could lead to a risk of rupture of the arterial aneurysm, so an intraoperative treatment must be done immediately.

It is generally acknowledged that, if the length of the proximal landing zone is less than 10 mm or/and the aneurysmal neck angle is more than 60°, the occurrence rate of the type I endoleak will rise obviously. Wherein the landing zone means a normal blood vessel at the proximal end and the distal end of enough length for adequately fitting with the stent. Such blood vessels are called landing zones (LZ), including the proximal LZ and the distal LZ. The aneurysmal neck angle refers to the angle of the medial axis of the aneurysmal neck and the medial axis of the aortic trunk.

At present, the treatments for type I endoleak found during the operation includes balloon angioplasty, adding a short stent graft or bare stent, or embolotherapy using cyanoacrylate, Onyx glue, spring ring or fibrin glue. Such treatments can deal with most type I endoleak, but may be difficult to perform in some situations, such as a very short proximal landing zone in abdominal aortic aneurysm, in which the adding of a short stent graft to the proximal end could influence the blood-supply of the renal artery.

Maldonado et al. summarize the effect of the above-mentioned treatment: the success rate of the embolization agent cyanoacrylate is 92.3%, the success rate of the short stent graft to the proximal end is 80%, and the success rate of the spring ring is 75%. No matter which treatment is used, the problem of success rate and increase of medical cost and operation time will not disappear. Moreover, the increase of the operation time will lead to a higher risk of infection during and after the operation, and the increase of the medical cost will lead to more financial burden on patients and more resource utilization of the society.

SUMMARY OF THE INVENTION

In consideration of such defects of above-mentioned prior art, the technical problem which the present invention aiming at is to redesign the stent used in endovascular graft exclusion, so as to avoid the occurrence of endoleak.

The present invention provide such solutions:

An endoleak preventing stent graft system, comprising:

a metal mesh support layer fit for the shape of said artery blood vessel;

a cover film layer touching said metal mesh support layer; and a flexible mesh layer or villus layer or sponge layer positioned outside said cover film layer, said flexible mesh layer or villus layer or sponge layer fills up the gap formed between said cover film layer and the inwall of said artery blood vessel under the effect of the flexibility of itself.

The related structures are:

<Structure 1>

An endoleak preventing stent graft system, comprising:

a metal mesh support layer fit for the shape of said artery blood vessel;

a cover film layer covering the surface of said metal mesh support layer; and a flexible mesh layer positioned outside said cover film layer, said flexible mesh layer fills up the gap formed between said cover film layer and the inwall of said artery blood vessel under the effect of the flexibility of itself.

Furthermore, the endoleak preventing stent graft system described in structure 1, comprising:

a metal mesh support layer fit for the shape of said artery blood vessel;

a cover film layer covering on said metal mesh support layer; and a flexible mesh layer positioned outside said cover film layer, said flexible mesh layer fills up the gap formed between said cover film layer and the inwall of said artery blood vessel under the effect of the flexibility of itself.

Furthermore, the type I endoleak preventing stent graft system with a sponge structure optimized on circumferential stress described in structure 1, comprising:

a metal mesh support layer fit for the shape of said artery blood vessel;

a cover film layer covering on said metal mesh support layer; and a flexible mesh layer positioned outside said cover film layer at the proximal end or positioned outside said cover film layer at both the proximal end and the distal end, said flexible mesh layer fills up the gap formed between said cover film layer and the inwall of said artery blood vessel under the effect of the flexibility of itself.

Furthermore, the type I endoleak preventing stent graft system with a sponge structure optimized on circumferential stress described in structure 1, wherein the thickness of said flexible mesh layer is within the range of 1 mm~5 mm.

Furthermore, the type I endoleak preventing stent graft system with a sponge structure optimized on circumferential stress described in structure 1, wherein said flexible mesh layer does not cover over the edges of both ends of said metal mesh support layer and said cover film layer.

Furthermore, the type I endoleak preventing stent graft system with a sponge structure optimized on circumferential stress described in structure 1, wherein said flexible mesh layer is made from any material performing a function of adsorption of blood platelet and a function of starting the blood clotting mechanism.

Furthermore, the type I endoleak preventing stent graft system with a sponge structure optimized on circumferential stress described in structure 1, wherein the material of said flexible mesh layer is poly (lactic-glycolic acid) PGLA.

Furthermore, the type I endoleak preventing stent graft system with a sponge structure optimized on circumferential stress described in structure 1, wherein said flexible mesh layer is formed by plural prisms with polyhedral shape.

Furthermore, the type I endoleak preventing stent graft system with a sponge structure optimized on circumferential stress described in structure 1, wherein said flexible mesh layer is formed by plural polyhedrons.

Furthermore, the type I endoleak preventing stent graft system with a sponge structure optimized on circumferential stress described in structure 1, wherein a part of said polyhedrons or all of said polyhedrons are hollowed out.

Furthermore, the type I endoleak preventing stent graft system with a sponge structure optimized on circumferential stress described in structure 1, wherein said polyhedron is elongated triangular bipyramid.

Furthermore, the type I endoleak preventing stent graft system with a sponge structure optimized on circumferential stress described in structure 1, wherein the long axis of said elongated triangular bipyramid is not parallel to the long axis of said type I endoleak preventing stent graft system with a sponge structure optimized on circumferential stress.

Furthermore, the type I endoleak preventing stent graft system with a sponge structure optimized on circumferential stress described in structure 1, wherein the long axis of said elongated triangular bipyramid is perpendicular to the long axis of said type I endoleak preventing stent graft system with a sponge structure optimized on circumferential stress.

Furthermore, the type I endoleak preventing stent graft system with a sponge structure optimized on circumferential stress described in structure 1, wherein said elongated triangular bipyramids are distributed to surround outside said cover film layer and are interlaced with each other to form a multilayer structure.

Furthermore, the type I endoleak preventing stent graft system with a sponge structure optimized on circumferential stress described in structure 1, wherein said polyhedrons or said prisms with polyhedral shape are distributed to surround outside said cover film layer and are interlaced with each other to form a multilayer structure.

<Structure 2>

An endoleak preventing stent graft system, comprising:
a metal mesh support layer fit for the shape of said artery blood vessel;
a cover film layer covering the surface of said metal mesh support layer; and
a flexible mesh layer positioned outside said cover film layer, said flexible mesh layer fills up the gap formed between said cover film layer and the inwall of said artery blood vessel under the effect of the flexibility of itself.

Furthermore, the endoleak preventing stent graft system described in structure 2, comprising:
a metal mesh support layer fit for the shape of said artery blood vessel;
a cover film layer covering on said metal mesh support layer; and
a flexible mesh layer positioned outside said cover film layer, said flexible mesh layer fills up the gap formed between said cover film layer and the inwall of said artery blood vessel under the effect of the flexibility of itself.

Furthermore, the endoleak preventing stent graft system described in structure 2, used for preventing the endoleaks except for type II endoleak, comprising:
a metal mesh support layer fit for the shape of the artery blood vessel;
a cover film layer covering on said metal mesh support layer; and
a flexible mesh layer covering outside the whole stent, said flexible mesh layer fills up the gap formed between said cover film layer and the inwall of said artery blood vessel under the effect of the flexibility of itself.

Furthermore, the endoleak preventing stent graft system described in structure 2, wherein the thickness of said flexible mesh layer is within the range of 1 mm~5 mm.

Furthermore, the endoleak preventing stent graft system described in structure 2, wherein said flexible mesh layer does not cover over the edges of both ends of said metal mesh support layer and said cover film layer.

Furthermore, the endoleak preventing stent graft system described in structure 2, wherein said flexible mesh layer is made from any material performing a function of adsorption of blood platelet and a function of starting the blood clotting mechanism.

Furthermore, the endoleak preventing stent graft system described in structure 2, wherein the material of said flexible mesh layer is poly (lactic-glycolic acid) PGLA.

Furthermore, the endoleak preventing stent graft system described in structure 2, wherein said flexible mesh layer is formed by plural prisms with polyhedral shape.

Furthermore, the endoleak preventing stent graft system described in structure 2, wherein said flexible mesh layer is formed by plural polyhedrons.

Furthermore, the endoleak preventing stent graft system described in structure 2, wherein a part of said polyhedrons or all of said polyhedrons are hollowed out.

Furthermore, the endoleak preventing stent graft system described in structure 2, wherein said polyhedron is elongated triangular bipyramid.

Furthermore, the endoleak preventing stent graft system described in structure 2, wherein the long axis of said elongated triangular bipyramid is not parallel to the long axis of said type I endoleak preventing stent graft system.

Furthermore, the endoleak preventing stent graft system described in structure 2, wherein the long axis of said elongated triangular bipyramid is perpendicular to the long axis of said type I endoleak preventing stent graft system.

Furthermore, the endoleak preventing stent graft system described in structure 2, wherein said elongated triangular bipyramids are distributed to surround outside said cover film layer and are interlaced with each other to form a multilayer structure.

Furthermore, the endoleak preventing stent graft system described in structure 2, wherein said polyhedrons or said prisms with polyhedral shape are distributed to surround outside said cover film layer and are interlaced with each other to form a multilayer structure.

<Structure 3>

An endoleak preventing stent graft system, comprising:

a metal mesh support layer fit for the shape of said artery blood vessel;

a cover film layer covering the surface of said metal mesh support layer; and a flexible mesh layer positioned outside said cover film layer, said flexible mesh layer fills up the gap formed between said cover film layer and the inwall of said artery blood vessel under the effect of the flexibility of itself.

Furthermore, the endoleak preventing stent graft system described in structure 3, comprising:

a metal mesh support layer fit for the shape of said artery blood vessel;

a cover film layer covering on said metal mesh support layer; and a flexible mesh layer positioned outside said cover film layer, said flexible mesh layer fills up the gap formed between said cover film layer and the inwall of said artery blood vessel under the effect of the flexibility of itself.

Furthermore, the endoleak preventing stent graft system described in structure 3, comprising:

a metal mesh support layer fit for the shape of said artery blood vessel;

a cover film layer positioned inside said metal mesh support layer; and a flexible mesh layer positioned outside said cover film layer, said flexible mesh layer fills up the gap formed between said cover film layer and the inwall of said artery blood vessel under the effect of the flexibility of itself.

Furthermore, the endoleak preventing stent graft system described in structure 3, a metal mesh support layer fit for the shape of said artery blood vessel;

a cover film layer positioned inside said metal mesh support layer; and a flexible mesh layer positioned outside said cover film layer at the proximal end or positioned outside said cover film layer at both the proximal end and the distal end, wherein said flexible mesh layer fills up the gap formed between said cover film layer and the inwall of said artery blood vessel under the effect of the flexibility of itself.

Furthermore, the endoleak preventing stent graft system described in structure 3, wherein the thickness of said flexible mesh layer is within the range of 1 mm~5 mm.

Furthermore, the endoleak preventing stent graft system described in structure 3, wherein said flexible mesh layer does not cover over the edges of both ends of said metal mesh support layer and said cover film layer.

Furthermore, the endoleak preventing stent graft system described in structure 3, wherein said flexible mesh layer is made from the material which can adsorb blood cells such as blood coagulation factor and blood platelet.

Furthermore, the endoleak preventing stent graft system described in structure 3, wherein the material of said flexible mesh layer is poly (lactic-glycolic acid) PGLA.

Furthermore, the endoleak preventing stent graft system described in structure 3, wherein said flexible mesh layer is formed by plural prisms with polyhedral shape.

Furthermore, the endoleak preventing stent graft system described in structure 3, wherein said flexible mesh layer is formed by plural polyhedrons.

Furthermore, the endoleak preventing stent graft system described in structure 3, wherein a part of said polyhedrons or all of said polyhedrons are hollowed out.

Furthermore, the endoleak preventing stent graft system described in structure 3, wherein said polyhedron is elongated triangular bipyramid.

Furthermore, the endoleak preventing stent graft system described in structure 3, wherein the long axis of said elongated triangular bipyramid is not parallel to the long axis of said type I endoleak preventing stent graft system.

Furthermore, the endoleak preventing stent graft system described in structure 3, wherein the long axis of said elongated triangular bipyramid is perpendicular to the long axis of said type I endoleak preventing stent graft system.

Furthermore, the endoleak preventing stent graft system described in structure 3, wherein said elongated triangular bipyramids are distributed to surround outside said cover film layer and are interlaced with each other to form a multilayer structure.

Furthermore, the endoleak preventing stent graft system described in structure 3, wherein said polyhedrons or said prisms with polyhedral shape are distributed to surround outside said cover film layer and are interlaced with each other to form a multilayer structure.

<Structure 4>

An endoleak preventing stent graft system, comprising:

a metal mesh support layer fit for the shape of said artery blood vessel;

a cover film layer covering the surface of said metal mesh support layer; and a flexible mesh layer positioned outside said cover film layer, said flexible mesh layer fills up the gap formed between said cover film layer and the inwall of said artery blood vessel under the effect of the flexibility of itself.

Furthermore, the endoleak preventing stent graft system described in structure 4, comprising:

a metal mesh support layer fit for the shape of said artery blood vessel;

a cover film layer covering on said metal mesh support layer; and a flexible mesh layer positioned outside said cover film layer, said flexible mesh layer fills up the gap formed between said cover film layer and the inwall of said artery blood vessel under the effect of the flexibility of itself.

Furthermore, the endoleak preventing stent graft system described in structure 4, used for preventing the endoleaks except for type II endoleak, comprising:

a metal mesh support layer fit for the shape of said artery blood vessel;

a cover film layer positioned inside said metal mesh support layer; and a flexible mesh layer covering outside the whole stent, said flexible mesh layer fills up the gap formed between said cover film layer and the inwall of said artery blood vessel under the effect of the flexibility of itself.

Furthermore, the endoleak preventing stent graft system described in structure 4, wherein the thickness of said flexible mesh layer is within the range of 1 mm~5 mm.

Furthermore, the endoleak preventing stent graft system described in structure 4, wherein said flexible mesh layer does not cover over the edges of both ends of said metal mesh support layer and said cover film layer.

Furthermore, the endoleak preventing stent graft system described in structure 4, wherein said flexible mesh layer is made from any material performing a function of adsorption of blood platelet and a function of starting the blood clotting mechanism.

Furthermore, the endoleak preventing stent graft system described in structure 4, wherein the material of said flexible mesh layer is poly (lactic-glycolic acid) PGLA.

Furthermore, the endoleak preventing stent graft system described in structure 4, wherein said flexible mesh layer is formed by plural prisms with polyhedral shape.

Furthermore, the endoleak preventing stent graft system described in structure 4, wherein said flexible mesh layer is formed by plural polyhedrons.

Furthermore, the endoleak preventing stent graft system described in structure 4, wherein a part of said polyhedrons or all of said polyhedrons are hollowed out.

Furthermore, the endoleak preventing stent graft system described in structure 4, wherein said polyhedron is elongated triangular bipyramid.

Furthermore, the endoleak preventing stent graft system described in structure 4, wherein the long axis of said elongated triangular bipyramid is not parallel to the long axis of said type I endoleak preventing stent graft system.

Furthermore, the endoleak preventing stent graft system described in structure 4, wherein the long axis of said elongated triangular bipyramid is perpendicular to the long axis of said type I endoleak preventing stent graft system.

Furthermore, the endoleak preventing stent graft system described in structure 4, wherein said elongated triangular bipyramids are distributed to surround outside said cover film layer and are interlaced with each other to form a multilayer structure.

Furthermore, the endoleak preventing stent graft system described in structure 4, wherein said polyhedrons or said prisms with polyhedral shape are distributed to surround outside said cover film layer and are interlaced with each other to form a multilayer structure.

<Structure 5>

An endoleak preventing stent graft system, comprising:
a metal mesh support layer fit for the shape of said artery blood vessel;
a cover film layer covering the surface of said metal mesh support layer; and
a villus layer covering outside said cover film layer, said villus layer fills up the gap formed between said cover film layer and the inwall of said artery blood vessel under the effect of the flexibility of itself.

Furthermore, the endoleak preventing stent graft system described in structure 5, comprising:
a metal mesh support layer fit for the shape of said artery blood vessel;
a cover film layer covering on said metal mesh support layer; and
a villus layer positioned on said cover film layer, said villus layer fills up the gap formed between said cover film layer and the inwall of said artery blood vessel under the effect of the flexibility of itself.

Furthermore, the endoleak preventing stent graft system described in structure 5, comprising:
a metal mesh support layer fit for the shape of said artery blood vessel;
a cover film layer covering on said metal mesh support layer; and
a villus layer positioned outside said cover film layer at the proximal end or positioned outside said cover film layer at both the proximal end and the distal end, said villus layer fills up the gap formed between said cover film layer and the inwall of said artery blood vessel under the effect of the flexibility of itself,
wherein said villus layer comprises plural villi,
the shape of said villi is linear shape or spiral shape or dendriform shape.

Furthermore, the endoleak preventing stent graft system described in structure 5, wherein the diameter of said villi is 25 μm, the length of said villi is within the range of 2 mm~6 mm.

Furthermore, the endoleak preventing stent graft system described in structure 5, wherein said villi incline toward the distal end.

Furthermore, the endoleak preventing stent graft system described in structure 5, wherein said villus layer does not cover over the edges of both ends of said metal mesh support layer and said cover film layer.

Furthermore, the endoleak preventing stent graft system described in structure 5, wherein said villus layer is made from any material performing a function of adsorption of blood platelet and a function of starting the blood clotting mechanism.

Furthermore, the endoleak preventing stent graft system described in structure 5, wherein the material of said villus layer is poly (lactic-glycolic acid).

<Structure 6>

An endoleak preventing stent graft system, comprising:
a metal mesh support layer fit for the shape of said artery blood vessel;
a cover film layer covering the surface of said metal mesh support layer; and
a villus layer covering outside said cover film layer, said villus layer fills up the gap formed between said cover film layer and the inwall of said artery blood vessel under the effect of the flexibility of itself.

Furthermore, the endoleak preventing stent graft system described in structure 6, comprising:
a metal mesh support layer fit for the shape of said artery blood vessel;
a cover film layer covering on said metal mesh support layer; and a villus layer positioned on said cover film layer, said villus layer fills up the gap formed between said cover film layer and the inwall of said artery blood vessel under the effect of the flexibility of itself.

Furthermore, the endoleak preventing stent graft system described in structure 6, used for preventing the endoleaks except for type II endoleak, comprising:

a metal mesh support layer fit for the shape of said artery blood vessel;

a cover film layer covering on said metal mesh support layer; and a villus layer covering outside the whole stent, wherein said villus layer comprises plural villi, said villus layer fills up the gap formed between said cover film layer and the inwall of said artery blood vessel under the effect of the flexibility of itself, the shape of said villi is linear shape or spiral shape or dendriform shape.

Furthermore, the endoleak preventing stent graft system described in structure 6, wherein the diameter of said villi is 25 µm, the length of said villi is within the range of 2 mm~6 mm.

Furthermore, the endoleak preventing stent graft system described in structure 6, wherein said villi incline toward the distal end.

Furthermore, the endoleak preventing stent graft system described in structure 6, wherein said villus layer does not cover over the edges of both ends of said metal mesh support layer and said cover film layer.

Furthermore, the endoleak preventing stent graft system described in structure 6, wherein said villus layer is made from any material performing a function of adsorption of blood platelet and a function of starting the blood clotting mechanism.

Furthermore, the endoleak preventing stent graft system described in structure 6, wherein the material of said villus layer is poly (lactic-glycolic acid).

<Structure 7>

An endoleak preventing stent graft system, comprising:

a metal mesh support layer fit for the shape of said artery blood vessel;

a cover film layer covering the surface of said metal mesh support layer; and a villus layer covering outside said cover film layer, said villus layer fills up the gap formed between said cover film layer and the inwall of said artery blood vessel under the effect of the flexibility of itself.

Furthermore, the endoleak preventing stent graft system described in structure 7, used for preventing the type I endoleak, comprising:

a metal mesh support layer fit for the shape of said artery blood vessel;

a cover film layer covering the inner surface of said metal mesh support layer; and a villus layer positioned outside said cover film layer, said villus layer fills up the gap formed between said cover film layer and the inwall of said artery blood vessel under the effect of the flexibility of itself.

Furthermore, the endoleak preventing stent graft system described in structure 7, used for preventing the type I endoleak, comprising:

a metal mesh support layer fit for the shape of said artery blood vessel;

a cover film layer covering the inner surface of said metal mesh support layer; and a villus layer positioned outside said cover film layer at the proximal end or positioned outside said cover film layer at both the proximal end and the distal end, said villus layer fills up the gap formed between said cover film layer and the inwall of said artery blood vessel under the effect of the flexibility of itself, wherein said villus layer comprises plural villi, the shape of said villi is linear shape or spiral shape or dendriform shape.

Furthermore, the endoleak preventing stent graft system described in structure 7, wherein the diameter of said villi is 25 µm, the length of said villi is within the range of 2 mm~6 mm.

Furthermore, the endoleak preventing stent graft system described in structure 7, wherein said villi incline toward the distal end.

Furthermore, the endoleak preventing stent graft system described in structure 7, wherein said villus layer does not cover over the edges of both ends of said metal mesh support layer and said cover film layer.

Furthermore, the endoleak preventing stent graft system described in structure 7, wherein said villus layer is made from any material performing a function of adsorption of blood platelet and a function of starting the blood clotting mechanism.

Furthermore, the endoleak preventing stent graft system described in structure 7, wherein the material of said villus layer is poly (lactic-glycolic acid).

<Structure 8>

An endoleak preventing stent graft system, comprising:

a metal mesh support layer fit for the shape of said artery blood vessel;

a cover film layer covering the surface of said metal mesh support layer; and a villus layer covering outside said cover film layer, said villus layer fills up the gap formed between said cover film layer and the inwall of said artery blood vessel under the effect of the flexibility of itself.

Furthermore, the endoleak preventing stent graft system described in structure 8, used for preventing the type I endoleak, comprising:

a metal mesh support layer fit for the shape of said artery blood vessel;

a cover film layer covering the inner surface of said metal mesh support layer; and a villus layer positioned outside said cover film layer, said villus layer fills up the gap formed between said cover film layer and the inwall of said artery blood vessel under the effect of the flexibility of itself.

Furthermore, the endoleak preventing stent graft system described in structure 8, used for preventing the endoleaks except for type II endoleak, comprising:

a metal mesh support layer fit for the shape of said artery blood vessel;

a cover film layer covering the inner surface of said metal mesh support layer; and a villus layer covering outside the whole stent, said villus layer fills up the gap formed between said cover film layer and the inwall of said artery blood vessel under the effect of the flexibility of itself, wherein said villus layer comprises plural villi, the shape of said villi is linear shape or spiral shape or dendriform shape.

Furthermore, the endoleak preventing stent graft system described in structure 8, wherein the diameter of said villi is 25 µm, the length of said villi is within the range of 2 mm~6 mm.

Furthermore, the endoleak preventing stent graft system described in structure 8, wherein said villi incline toward the distal end.

Furthermore, the endoleak preventing stent graft system described in structure 8, wherein said villus layer does not cover over the edges of both ends of said metal mesh support layer and said cover film layer.

Furthermore, the endoleak preventing stent graft system described in structure 8, wherein said villus layer is made from any material performing a function of adsorption of blood platelet and a function of starting the blood clotting mechanism.

Furthermore, the endoleak preventing stent graft system described in structure 8, wherein the material of said villus layer is poly (lactic-glycolic acid).

<Structure 9>

An endoleak preventing stent graft system, used for preventing the endoleaks except for type II endoleak, comprising:

a metal mesh support layer fit for the shape of said artery blood vessel;

a cover film layer covering on said metal mesh support layer; and a sponge layer positioned outside said cover film layer, said sponge layer fills up the gap formed between said cover film layer and the inwall of said artery blood vessel under the effect of the flexibility of itself, Furthermore, the endoleak preventing stent graft system described in structure 9, wherein said sponge layer comprises plural even-distributed rhombus grids, and the longer diagonal of said rhombus is along with the direction of the blood flow.

The effect of the present invention:

According to the endoleak preventing stent graft system with a flexible mesh layer provided in the present invention, since the flexible mesh layer is set outside the cover film layer and the flexible mesh layer can fill up the gap formed between the cover film layer and the inwall under the effect of the flexibility of itself, the blood could be prevented to flush into the aneurysm cavity. Therefore the residual blood in the flexible mesh layer will clot after some time, thus the aneurysm cavity could be sealed completely and then reaches the steady state.

According to endoleak preventing stent graft system with a sponge structure provided in the present invention, since the sponge layer is set outside the cover film layer and the sponge layer can fill up the gap formed between the cover film layer and the inwall under the effect of the flexibility of itself, the blood could be prevented to flush into the aneurysm cavity. Therefore the residual blood in the sponge layer will clot after some time, thus the aneurysm cavity could be sealed completely and then reaches the steady state.

The flexible mesh layer or the sponge layer or the villus layer performs three functions, one is to perform as a physical barrier to slow down the blood flow so as to accelerate the blood clotting, and another is to perform chemical function that PGLA can adsorb blood cells such as blood coagulation factor and blood platelet so as to accelerate the blood clotting further. Meanwhile The flexible mesh layer or the sponge layer or the villus layer could also functions as a fibrosis basement.

Moreover, since the flexible mesh layer or the sponge layer or the villus layer covers all surface of the cover film layer, the stent could prevent not only type I endoleak but also type III to type IV endoleak. The type III endoleak is the endoleak caused by the rupture of the cover film layer. For traditional stent, the aneurysm cavity will connect with the blood flow directly when the cover film layer ruptures. While in the present invention, since the flexible mesh layer or the sponge layer or the villus layer is added, even the cover film layer ruptures, the flexible mesh layer or the sponge layer or the villus layer could obstruct the aneurysm cavity and the blood flow. Since the flexible mesh layer or the sponge layer or the villus layer is a kind of polyporous structure which can slow down the blood flow when the blood flush into, a fast flush of blood could be prevented to avoid the rupture of the aneurysm cavity. Meanwhile, since the blood flow slows down and the flexible mesh layer or the sponge layer or the villus layer can adsorb blood coagulation factor and blood platelet, the residual blood in the aneurysm cavity will clot soon. So after some time the aneurysm cavity will be sealed completely by the flexible mesh layer or the sponge layer or the villus layer and the clotted blood wherein. For the same reason, the type IV endoleak and type V endoleak could be prevented as well.

DETAILED DESCRIPTION OF THE INVENTION

There're many reasons cause type I endoleak, namely, there're many reasons cause the bad fit between the stent film and the landing zone of the blood vessel inwall and further lead to a blood leak to the aneurysm cavity from the proximal end or the distal end of the covered stent. The stent graft system with a sponge structure of the present invention can prevent all type I endoleaks caused by any reasons. In the embodiments described hereinafter, the atheromatous plaque, which could cause the bad fit between the stent film and the landing zone of the blood vessel inwall, is taken as an example for illustration.

Embodiments of the present invention will be described in detail herein below with reference to the figures for explaining the present invention.

Embodiment 1

Figure 1:
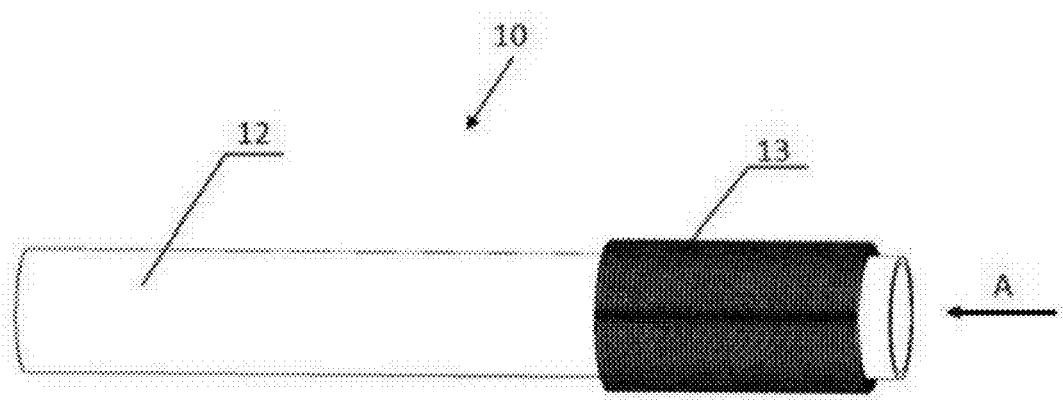
FIG. 1 is a whole structure illustration of the endoleak preventing stent graft system in the present invention.
Figure 2:
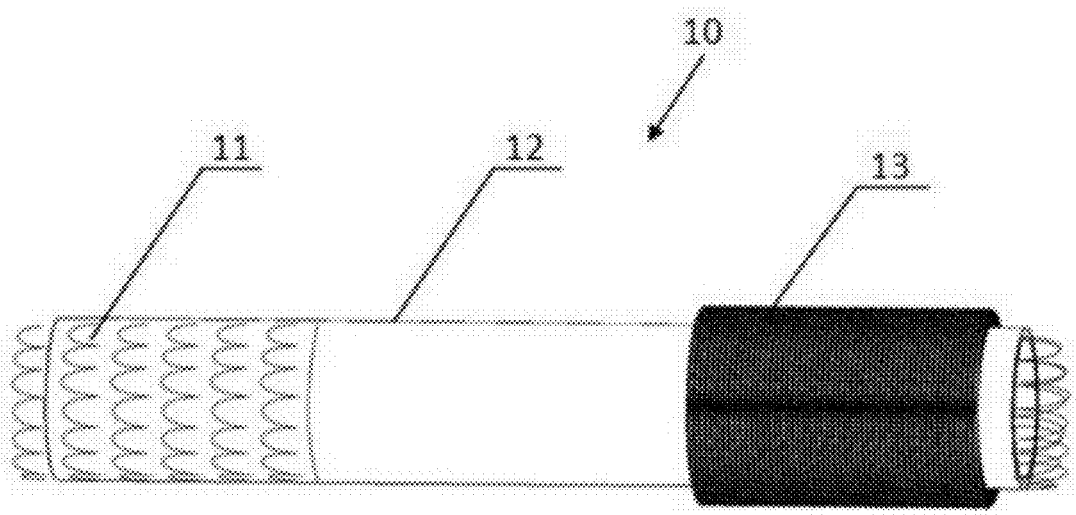
FIG. 2 is an inner structure illustration of the endoleak preventing stent graft system in the present invention.

FIG. 1 is a whole structure illustration of the endoleak preventing stent graft system in the present invention. FIG. 2 is an inner structure illustration of the endoleak preventing stent graft system in the present invention.

As shown in FIG. 1 and FIG. 2, a type I endoleak preventing stent graft system 10 with a sponge structure optimized on circumferential stress comprises a metal mesh support layer 11, a cover film layer 12 and a flexible mesh layer 13.

The metal mesh support layer 11 locates the most inner layer. The cover film layer 12 covers outside the metal mesh support layer 11. The flexible mesh layer 13 locates the outside layer of the cover film layer 12 at the proximal end. On the side towards the blood flow, namely the proximal end, the blood flow performs a strong impact force and flows against the gap propped by the atheromatous plaque, so the blood tends to flush into the gap. However, on the distal end, the gap opens along the direction of the blood flow, so the blood can hardly flush into the gap. Even there's a gap on the distal end, the blood will flow slowly there and will clot after some time, so there's much lower risk there. Therefore, the flexible mesh layer is no need to be set on the distal end of the type I endoleak preventing stent graft system 20 with a sponge structure optimized on circumferential stress, so as to save the cost.

The common used material of the cover film layer 12 is Dacron, also known as ethylene glycol terephthalate. The common used material of the flexible mesh layer 13 is poly (lactic-glycolic acid), abbreviated as PGLA. The PGLA material can perform an adsorption function of blood coagulation factor. The flexible mesh layer 13 is pasted onto the cover film layer.

Figure 3:
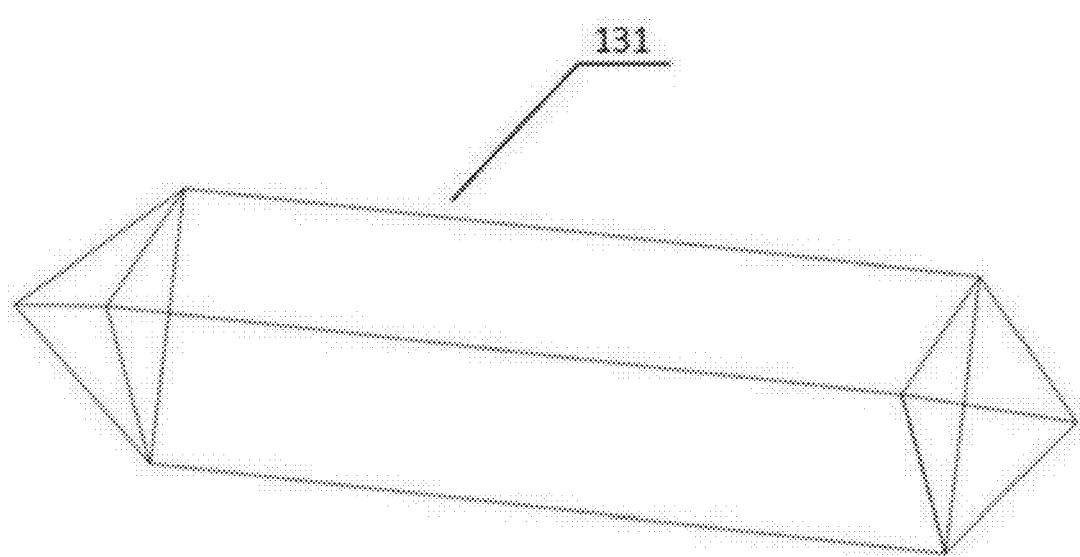
FIG. 3 is a structure illustration of the basic form unit of the endoleak preventing stent graft system in the present invention.

FIG. 3 is a structure illustration of the basic form unit of the endoleak preventing stent graft system in the present invention.

As shown in FIG. 3, a basic form unit 131 of the flexible mesh layer is formed by prisms with an elongated triangular bipyramid shape, which is hollowed out inside and on the prismatic surface. The basic form unit 131 is made from PGLA and is flexible.

Figure 4:
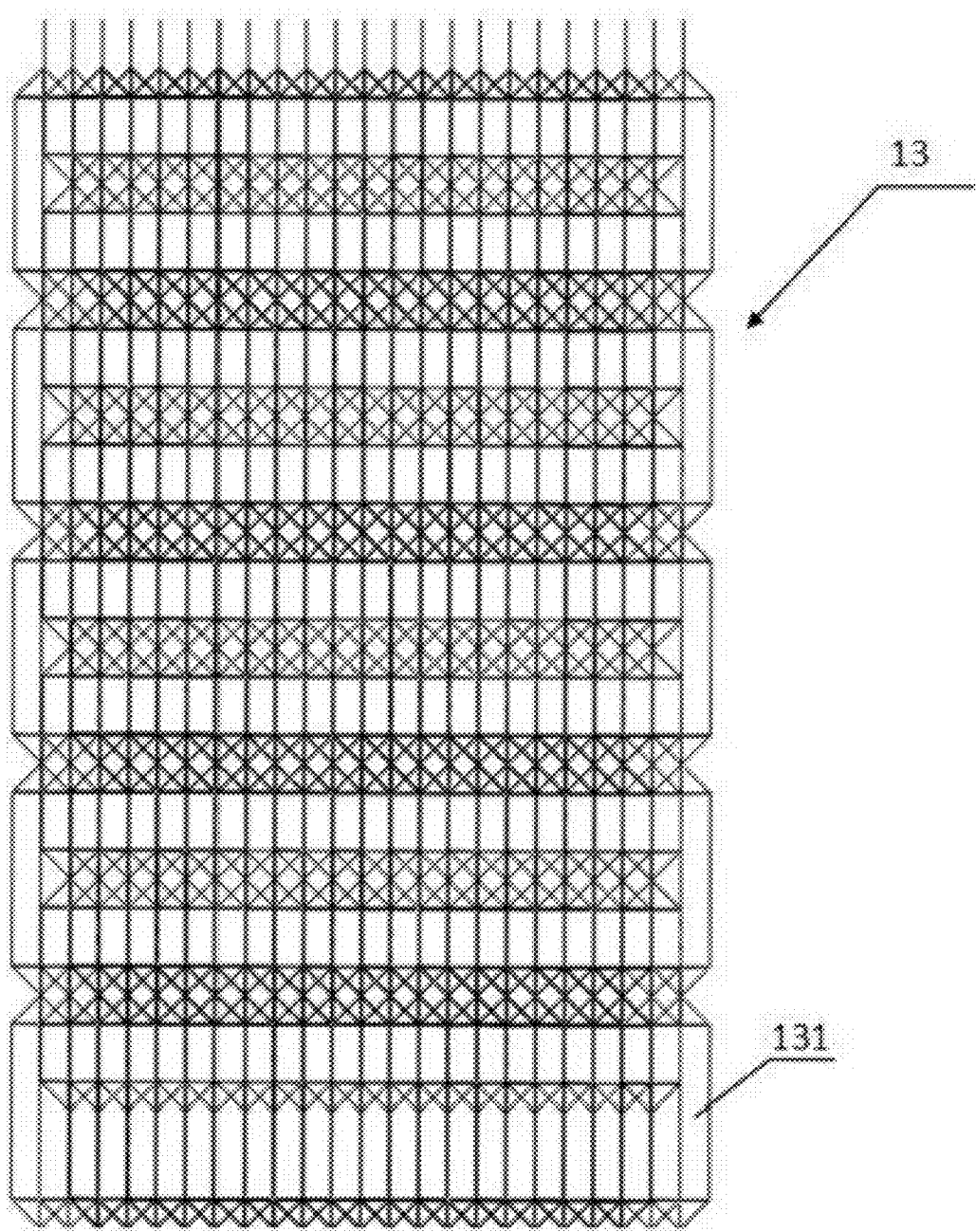
FIG. 4 is a partial cutaway view of the flexible mesh layer along the long axis direction of the stent of the endoleak preventing stent graft system in the present invention.

FIG. 4 is a partial cutaway view of the flexible mesh layer along the long axis direction of the stent of the endoleak preventing stent graft system in the present invention.

As shown in FIG. 4, plural basic form units 131 overlap each other and form a flexible mesh layer structure. The long axis of the basic form unit 131 is perpendicular to the central axis of the stent. The basic form units 131 are arrayed side by side to form a monolayer structure.

Figure 5:
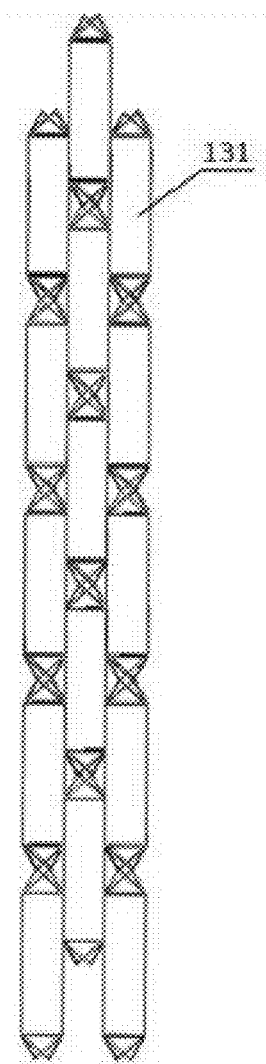
FIG. 5 is an interlacement structure illustration of the basic form units in the flexible mesh.

FIG. 5 is an interlacement structure illustration of the basic form units in the flexible mesh. The adjacent basic form units 131 at the junction positions of plural monolayer structures are interlaced with each other, so as to form a multilayer structure. Such multilayer structure forms a cylinder structure, which surrounds the proximal end of the type I endoleak preventing stent graft system with a sponge structure optimized on circumferential stress.

Figure 6:
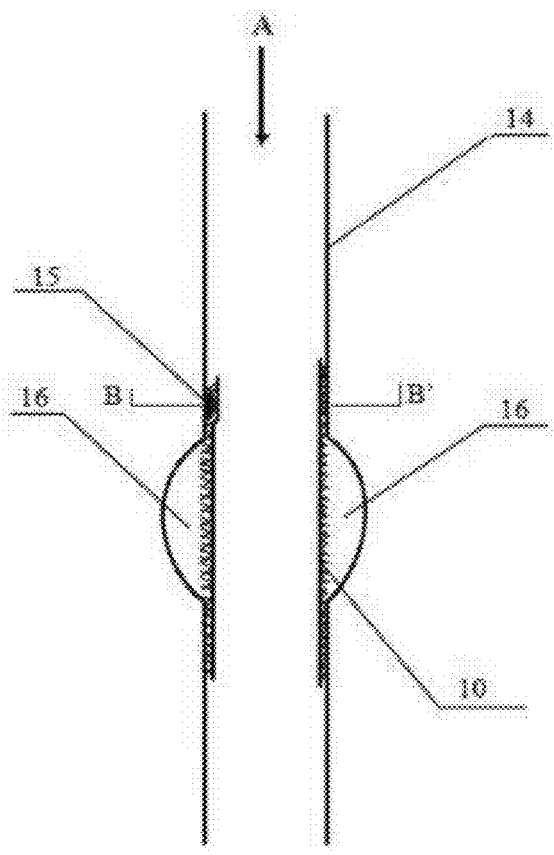
FIG. 6 is an implantation illustration of the endoleak preventing stent graft system into the blood vessel in the present invention.
Figure 7:
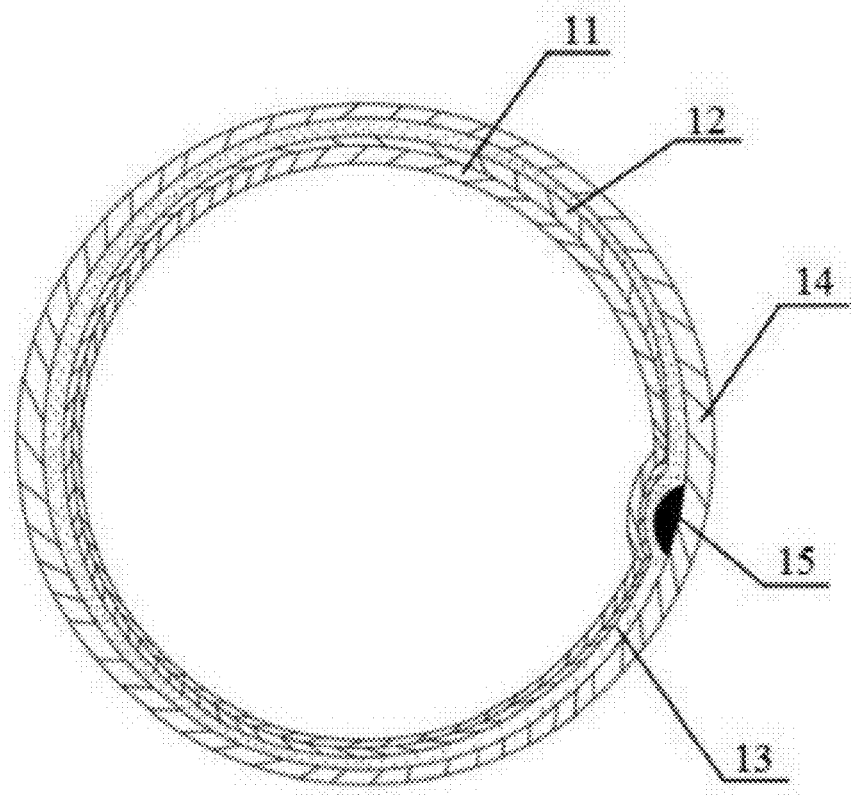
FIG. 7 is a BB' cutaway view of FIG. 6.

FIG. 6 is an implantation illustration of the endoleak preventing stent graft system into the blood vessel in the present invention. FIG. 7 is a BB' cutaway view of FIG. 6.

As shown in FIG. 6 and FIG. 7, the type I endoleak preventing stent graft system 10 with a sponge structure optimized on circumferential stress needs to be implanted into the blood vessel where the arterial aneurysm occurs. There is an atheromatous plaque 15 on the vessel wall of an artery blood vessel 14 near by an aneurysm cavity 16. The atheromatous plaque 15 protrudes inward, and props the metal mesh support layer 11 and cover film layer 12 of the type I endoleak preventing stent graft system 10, therefore a gap forms between the cover film layer 12 and the blood vessel inwall.

Since the flexible mesh layer 13 is flexible, the flexible mesh layer 13 can fill up the gap. Furthermore, since there's much void in the flexible mesh layer 13, the blood flow in the gap filled with the flexible mesh layer will slow down greatly. Meanwhile, under the effect of blood coagulation factor in the blood, the residual blood in the gap, which is filled with the flexible mesh layer 13, will clot after some time and seal the gap.

There's another harmful effect of the existence of the gap. Since the gap is always flushed by the blood, the endothelial cells of the blood vessels cannot grow into the stent, which makes the endothelial cells cannot cover edges of the stent and further cannot extend to a whole with the blood vessel endothelium. However, after the type I endoleak preventing stent graft system 10 with a sponge structure optimized on circumferential stress of the present embodiment is implanted, since the blood flow in the gap slows down, there will be enough time for the endothelial cells of the blood vessels near by the stent to grow into the inner surface of the type I endoleak preventing stent graft system 10 with a sponge structure optimized on circumferential stress. The endothelial cells can finally cover the inner surface of the stent and become a whole with the blood vessel endothelium at both ends. Thus the stent can reach a steady state, and the blood will not flush into the aneurysm cavity any more. Furthermore, after the residual blood in the aneurysm cavity clots, the aneurysm cavity also reaches a steady state, so that the endothelial cells can grow in the aneurysm cavity and the aneurysm cavity will not rupture easily.

In FIG. 1 and FIG. 6, direction A refers to the direction of the blood flow. The end near by the direction A is the proximal end, and the end away from the direction A is the distal end. The length of the flexible mesh layer 13 is not longer than the distance between the upper edge and the bottom edge of the metal mesh support layer and the cover film layer. Such a design can avoid the flexible mesh layer stretching out from the edges of the type I endoleak preventing stent graft system 10 with a sponge structure optimized on circumferential stress, which may cause blood clotting there, may form thrombus and may further embolize the vessels.

The implanting method of the type I endoleak preventing stent graft system with a sponge structure optimized on circumferential stress is:

The implanting method No. 1 of the type I endoleak preventing stent graft system 10 with a sponge structure optimized on circumferential stress:

Set the type I endoleak preventing stent graft system 10 with a sponge structure optimized on circumferential stress onto a stents conveyor, and then convey it to the vasculopathy position by the stents conveyor. Release the self-expanding stent gradually by a release device to make the type I endoleak preventing stent graft system 10 with a sponge structure optimized on circumferential stress seal the blood flow in the aneurysm cavity, and then pull the conveyor out. So that the stent can be placed at the vasculopathy position to achieve the purpose of sealing the aneurysm cavity.

During the operation, a digital subtraction angiography (DSA) can be used for monitoring the whole process inside human body that the conveyor enters the aorta from the arteriole and finally reaches the aneurysm cavity.

The implanting method No. 2 of the type I endoleak preventing stent graft system 10 with a sponge structure optimized on circumferential stress:

Set the type I endoleak preventing stent graft system 10 with a sponge structure optimized on circumferential stress onto a balloon catheter, and then convey it to the vasculopathy position by the balloon catheter. Inject fluid by a force pump to expand the balloon, further to expand the type I endoleak preventing stent graft system 10 with a sponge structure optimized on circumferential stress so as to seal the aneurysm cavity. Then pull the conveyor out. So that the stent can be placed at the vasculopathy position to achieve the purpose of sealing the aneurysm cavity.

During the operation, an X-ray radiography can be used for monitoring the whole process inside human body that the conveyor enters the aorta from the arteriole and finally reaches the aneurysm cavity.

Function and Effects of the Embodiment 1

According to the type I endoleak preventing stent graft system with a sponge structure optimized on circumferential stress provided in the embodiment 1, since the flexible mesh layer is set outside the cover film layer and the flexible mesh layer can fill up the gap formed between the cover film layer and the inwall under the effect of the flexibility of itself, in the case that there's an atheromatous plaque on the vessel wall, the flexible cover film layer could fill up the gap formed between the inwall and the cover film layer propped by atheromatous plaque, and then could prevent the blood to flush into the aneurysm cavity. Therefore the residual blood in the flexible mesh layer will clot after some time, thus the aneurysm cavity could be sealed completely and then reaches the steady state.

The polyporous flexible mesh layer performs three functions, one is to perform as a physical barrier to slow down the blood flow so as to accelerate the blood clotting, and another is to perform chemical function that PGLA can adsorb blood cells such as blood coagulation factor and blood platelet so as to accelerate the blood clotting further.

Meanwhile the mesh structure performs as a fibrosis basement, which could promote fibroblast to grow into and stabilize the aneurysm cavity.

Moreover, since the length of the flexible mesh layer 13 is not longer than the distance between the upper edge and the bottom edge of the metal mesh support layer and the cover film layer, it could be avoid that the flexible mesh layer stretches out from the edges of the type I endoleak preventing stent graft system 10 with a sponge structure optimized on circumferential stress, which may cause blood clotting there, may form thrombus and may further embolize the vessels.

Moreover, since the shape of the basic form unit of flexible mesh layer is elongated triangular bipyramid whose long axis is perpendicular to the long axis of the stent, the elongated triangular bipyramid can perform a deformation more easily when bearing a force performed by the blood vessel wall and perpendicular to the long axis direction of the stent, so that the leak-proofness which the sponge layer performs on the type I endoleak occurring between the stent and the blood vessel wall could be tighter.

Embodiment 2

In the present embodiment 2, structures same as those of the above embodiment are given to the same numbers, and the same description is omitted.

Figure 8:
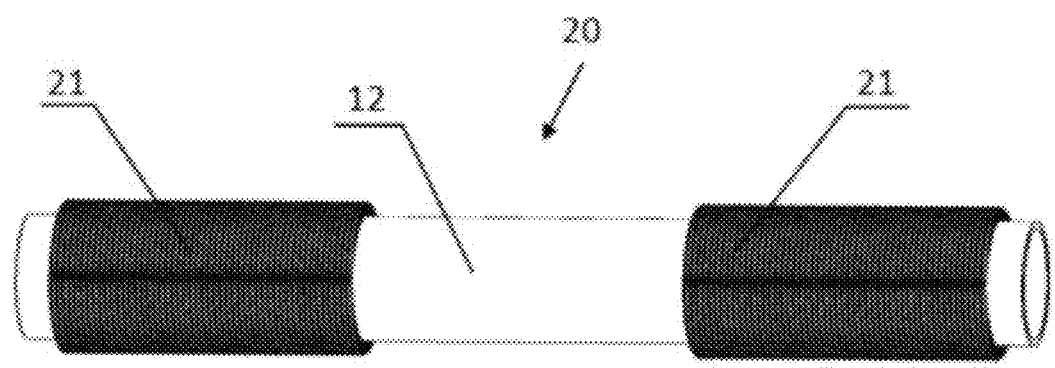
FIG. 8 is a structure illustration of the endoleak preventing stent graft system with flexible mesh layers on proximal end and distal end.

FIG. 8 is a structure illustration of the endoleak preventing stent graft system with flexible mesh layers on proximal end and distal end.

As shown in FIG. 8, a flexible mesh layer 21 covers both ends of the type I endoleak preventing stent graft system 20 with a sponge structure optimized on circumferential stress. The advantage of setting the flexible mesh layer on both ends is to further prevent the type I endoleak occur at the distal end, even such a situation may hardly occur. Such a design could enforce the safety of the stent.

Obviously, the flexible mesh layer can also be formed by prisms with other polyhedral shapes, such as hexahedron and tetrahedron. The preferred shape is elongated triangular bipyramid, a kind of enneahedron, used in the present embodiment.

Obviously, it is preferred that the long axis of the basic form unit is perpendicular to the central axis of the stent, while the two directions can be set as other angles. Of cause the closer the angle is to the vertical, the better the effect.

Moreover, the cover film layer can also cover the inner surface of the metal mesh support layer, so that the metal mesh support layer and the cover film layer connects with each other directly. Such a layer arrangement can also achieve the effects of the present invention.

Embodiment 3

In the present embodiment 3, structures same as those of the above embodiment are given to the same numbers, and the same description is omitted.

Figure 9:
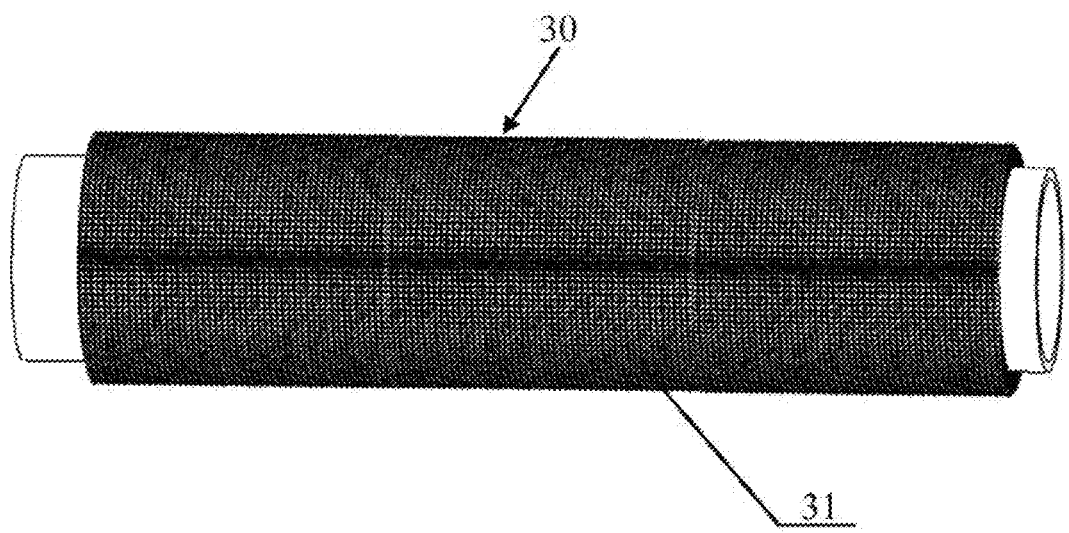
FIG. 9 is a structure illustration of the endoleak preventing stent graft system with all surface covered by a flexible mesh layer.

FIG. 9 is a structure illustration of the endoleak preventing stent graft system with all surface covered by a flexible mesh layer.

As shown in FIG. 9, a flexible mesh layer 31 covers the outermost layer of an endoleak preventing stent graft with a sponge structure 30.

FIG. 3 is a structure illustration of the basic form unit of the mesh structure of the endoleak preventing stent graft with a sponge structure in the present invention.

As shown in FIG. 3, a basic form unit 131 of the flexible mesh layer is formed by prisms with an elongated triangular bipyramid shape, which is hollowed out inside and on the prismatic surface.

The material of the flexible mesh layer should comprise the adsorption function of blood cells such as blood coagulation factor and blood platelet. For example, the material could be PGLA.

FIG. 4 is a structure illustration of the mesh structure of the endoleak preventing stent graft with the sponge structure in the present invention.

As shown in FIG. 4, plural basic form units 131 overlap each other and form a flexible mesh piece structure 132. The long axis of the basic form unit 131 is perpendicular to the central axis of the stent. The basic form units 131 are arrayed side by side to form a monolayer structure, as shown in FIG. 5.

FIG. 5 is a partial cutaway view of FIG. 4.

The adjacent basic form units 131 at the junction positions of plural monolayer structures are interlaced with each other, so as to form a multilayer structure. Such multilayer structure forms a cylinder structure, which surrounds the endoleak preventing stent graft with a sponge structure.

Since the shape of the basic form unit of flexible mesh layer is elongated triangular bipyramid whose long axis is perpendicular to the long axis of the stent, the elongated triangular bipyramid can perform a deformation more easily when bearing the force performed by the blood vessel wall and perpendicular to the long axis direction of the stent, so that the leak-proofness which the sponge layer performs on the type I endoleak occurring between the stent and the blood vessel wall could be tighter.

Obviously, the flexible mesh layer can also be formed by prisms with other polyhedral shapes, such as hexahedron and tetrahedron. The preferred shape is elongated triangular bipyramid, a kind of enneahedron, used in the present embodiment.

Obviously, it is preferred that the long axis of the basic form unit is perpendicular to the central axis of the stent, while the two directions can be set as other angles. Of course the closer to the vertical the angle is, the better the effect.

In the embodiment 3, since the sponge layer covers all surface of the stent, the stent can prevent type I endoleak occurs at both the proximal end and the distal end.

Moreover, since the flexible mesh layer covers all surface of the cover film layer, the stent could prevent not only type I endoleak but also type III to type IV endoleak. The type III endoleak is the endoleak caused by the rupture of the cover film layer. For traditional stent, the aneurysm cavity will connect with the blood flow directly when the cover film layer ruptures. While in the present invention, since the flexible mesh layer is added, even the cover film layer ruptures the flexible mesh layer could obstruct the aneurysm cavity and the blood flow. Since the flexible mesh layer is a kind of polyporous structure which can slow down the blood flow when the blood flush into, a fast flush of blood could be prevented to avoid the rupture of the aneurysm cavity. Meanwhile, since the blood flow slows down and the flexible mesh layer can adsorb blood coagulation factor and blood platelet, the residual blood in the aneurysm cavity will clot soon. So after some time the aneurysm cavity will be sealed completely by the flexible mesh layer and the clotted blood wherein. For the same reason, the type IV endoleak and type V endoleak could be prevented as well.

Moreover, the cover film layer can also cover the inner surface of the metal mesh support layer, so that the metal mesh support layer and the cover film layer connects with each other directly. Such a layer arrangement can also achieve the effects of the present invention.

Embodiment 4

The endoleak preventing stent graft with the sponge structure in the present invention comprises a metal mesh support layer fit for the artery blood vessel; cover film layer positioned inside said metal mesh support layer; flexible mesh layer covering all external surfaces of the stent. Such a design could enforce the safety of the stent.

Obviously, the flexible mesh layer can also be formed by prisms with other polyhedral shapes, such as hexahedron and tetrahedron. The preferred shape is elongated triangular bipyramid, a kind of enneahedron, used in the present embodiment.

Obviously, it is preferred that the long axis of the basic form unit is perpendicular to the central axis of the stent, while the two directions can be set as other angles. Of course the closer to the vertical the angle is, the better the effect.

Embodiment 5

The endoleak preventing stent graft with the sponge structure in the present invention comprises a metal mesh support layer fit for the artery blood vessel; a cover film layer positioned inside said metal mesh support layer; a flexible mesh layer covering the external surfaces of the proximal end only or both the proximal end and the distal end of the stent, wherein said flexible mesh layer fills up the gap formed between the cover film layer and said artery blood vessel under the effect of the flexibility of itself.

The advantage of setting the flexible mesh layer on both ends is to further prevent the type I endoleak occur at the distal end. Although such a situation may hardly occur, the above design could enforce the safety of the stent.

Obviously, the flexible mesh layer can also be formed by prisms with other polyhedral shapes, such as hexahedron and tetrahedron. The preferred shape is elongated triangular bipyramid, a kind of enneahedron, used in the present embodiment.

Obviously, it is preferred that the long axis of the basic form unit is perpendicular to the central axis of the stent, while the two directions can be set as other angles. Of course the closer to the vertical the angle is, the better the effect.

Embodiment 6

Figure 10:
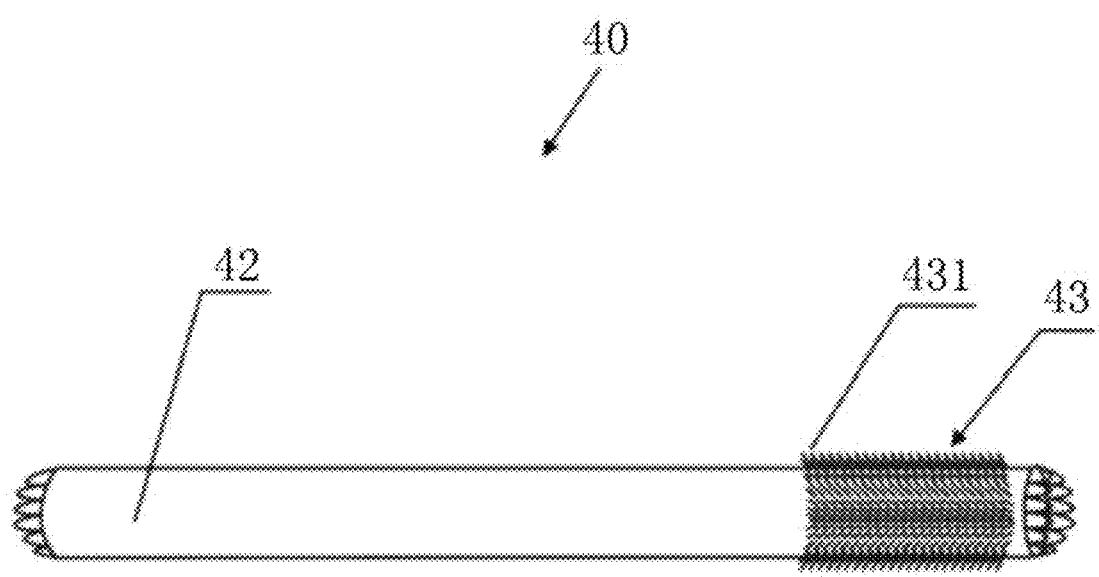
FIG. 10 is a whole structure illustration of an endoleak preventing stent graft with a villus layer in the present invention.
Figure 11:
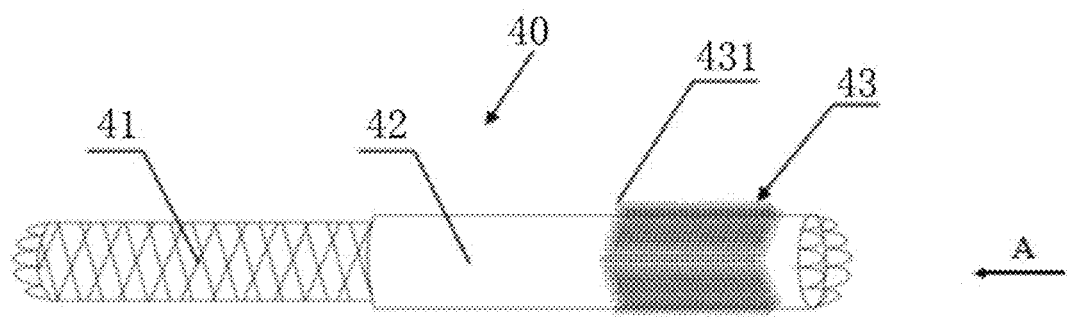
FIG. 11 is an inner structure illustration of an endoleak preventing stent graft with a villus layer in the present invention.

FIG. 10 is a whole structure illustration of an endoleak preventing stent graft with a villus layer in the present invention, FIG. 11 is an inner structure illustration of an endoleak preventing stent graft with a villus layer in the present invention.

As shown in FIG. 10 and FIG. 11, the endoleak preventing stent graft 40 with a villus layer comprises a metal mesh support layer 41, a cover film layer 42 and a villus layer 43.

The metal mesh support layer 41 locates the most inner layer, on which the cover film layer 42 covers outside. The villus layer 43 locates the outside layer of the cover film layer 42 at the proximal end.

The common used material of the cover film layer 42 is Dacron, also known as ethylene glycol terephthalate. The villus layer 43 could be formed by plural villi, with linear shape or spiral shape or dendriform shape, covering the cover film layer. The material of the cover film layer is poly (lactic-glycolic acid), abbreviated as PGLA. One end of the villus 431 is connected on the surface of the cover film layer 42, and the other end stretches outward. The PGLA material can perform an adsorption function of blood cells such as blood coagulation factor and blood platelet. The villus layer 43 could be planted onto the cover film layer.

As shown in FIG. 10, direction A refers the direction of the blood flow. The end near by the direction A is the proximal end, and the end away from the direction A is the distal end. And the distal end means the end away from the heart. Although the inclined directions of each villus in the villus layer 43 are not completely same, the villi all incline toward the distal direction. The length of the villus layer 43 is not over the proximal edge of the metal mesh support layer and the cover film layer. Such a design can avoid the villi stretching out from the edges of the type I endoleak preventing stent graft system with a villus layer 10, which may cause blood clotting there, may form thrombus and may further embolize the vessels under the flush of blood. If there's no villi stretching out the edges, the blood clotting will occur only between the stent and the blood vessel wall, and no thrombus will enter the vessels.

In the case that the villi in the villus layer of the endoleak preventing stent graft with a villus layer are spiral shape or dendriform shape, the spiral villi or the dendriform villi could form a mesh structure more firming than the linear villi, so the obstruction effect of blood could be stronger and the blood clotting could be accelerated.

Figure 12:
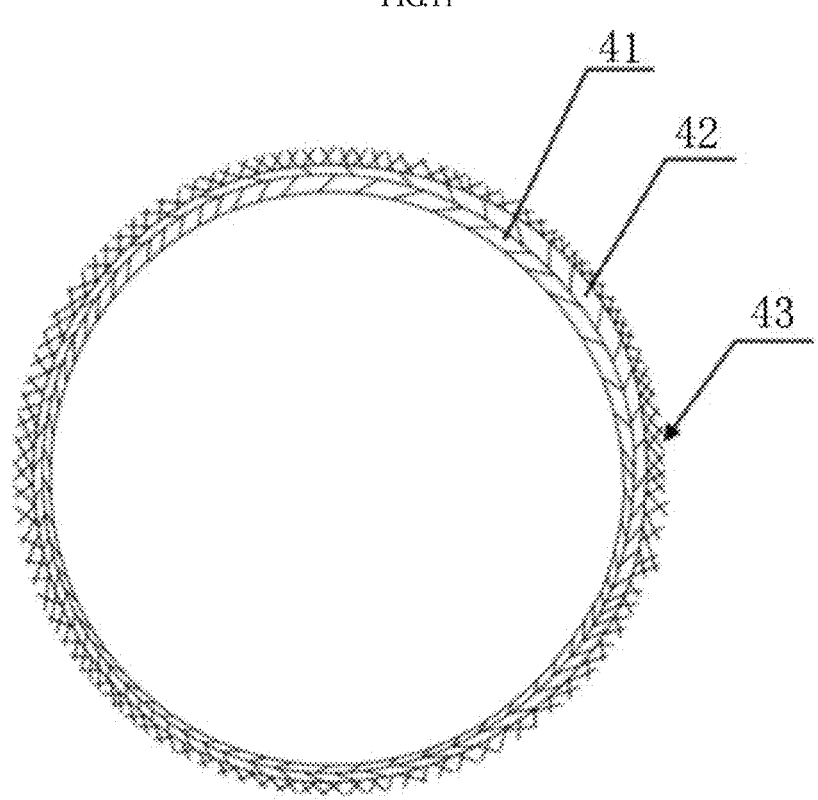
FIG. 12 is a cutaway view of the endoleak preventing stent graft with the villus layer in the present invention.

FIG. 12 is a cutaway view of the endoleak preventing stent graft with the villus layer in the present invention.

As shown in FIG. 12, the flexible villi stretch out of the cover film layer in different directions, while all the villi incline toward the distal direction. In the case of spiral villi or dendriform villi, the actual mesh structure is more firming and complex than shown in FIG. 12.

The implantation of the endoleak preventing stent graft with the villus layer in the present invention could be referred by FIG. 6, while FIG. 7 is a B-B cutaway view of FIG. 6.

As shown in FIG. 6 and FIG. 7, the endoleak preventing stent graft with the villus layer needs to be implanted into the blood vessel where the arterial aneurysm occurs. There is an atheromatous plaque 15 on the vessel wall of an artery blood vessel 14 near by an aneurysm cavity 16. The atheromatous plaque 15 protrudes inward, and props the villi in the villus layer of the endoleak preventing stent graft with the villus layer 40. Obviously, if the atheromatous plaque is large enough, the metal mesh support layer 41 will be propped as well. A gap forms between the cover film layer 42 and the blood vessel inwall.

Since the villi 431 in villus layer 43 are flexible, the villus can fill up the gap. And since the villus will perform a deformation when bearing the force from the inwall and the bending directions of the deformation are different, a mesh structure will be formed in the gap. The blood flow in the gap filled with the villi will slow down greatly. Meanwhile, under the effect of blood coagulation factor in the blood, the residual blood in the gap which is filled with the villi will clot after some time and seal the gap.

There's another harmful effect of the existence of the gap. Since the gap is always flushed by the blood, the endothelial cells of the blood vessels cannot grow into the stent, which makes the endothelial cells cannot cover edges of the stent and further cannot extend to a whole with the blood vessel endothelium. However, after the type I endoleak preventing stent graft system 40 with a villus layer of the present embodiment is implanted, since the blood flow in the gap slows down, there will be enough time for the endothelial cells of the blood vessels near by the stent to grow into the inner surface of the type I endoleak preventing stent graft system 40 with a villus layer. The endothelial cells can finally cover the inner surface of the stent and become a whole with the blood vessel endothelium at both ends. Thus the stent can reach a steady state, and the blood will not flush into the aneurysm cavity any more. Furthermore, after the residual blood in the aneurysm cavity clots, the aneurysm cavity also reaches a steady state, so that the endothelial cells can grow in the aneurysm cavity and the aneurysm cavity will not rupture easily.

The biodegradation time of PGLA could be influenced by many factors, so there're many methods to adjust the biodegradation time. One of the methods is provided hereinafter: adjust the biodegradation time by adjusting the ratio of two monomer, glycolide and lactide, in synthetic reaction. As the molar ratio of glycolide increases, the biodegradation rate increases as well. When the molar ratio is glycolide:lactide=50:50, the biodegradation time is 50~60 days. And when the molar ratio is glycolide:lactide=85:15, the biodegradation time is 150 days. The time period that the blood starts clotting and the fibroblast grows in until the fibrosis completes is within two weeks, so the biodegradation time is preferred 50~150 days for an enough time to ensure that the aneurysm cavity and the endoleak part could reach the steady state. So that the sealing of the type I endoleak will not be influenced by the short biodegradation time of PGLA.

The length of the villi in embodiment 1 could be set as any length within the range of 3.0~4.0 mm.

The implanting method of the endoleak preventing stent graft 40 with a villus layer:

Set the endoleak preventing stent graft 40 with a villus layer onto a stents conveyor, and then convey it to the vasculopathy position by the stents conveyor. Release the self-expanding stent gradually by a release device to make the endoleak preventing stent graft 40 with a villus layer seal the blood flow in the aneurysm cavity, and then pull the conveyor out. So that the stent can be placed at the vasculopathy position to achieve the purpose of sealing the aneurysm cavity.

During the operation, the digital subtraction angiography (DSA) can be used for monitoring the whole process inside human body that the conveyor enters the aorta from the arteriole and finally reaches the aneurysm cavity.

Function and Effects of the Embodiment 6

According to the endoleak preventing stent graft with a villus layer provided in the embodiment 6, since the villus layer is set outside the cover film layer and the villus layer can fill up the gap formed between the cover film layer and the inwall under the effect of the flexibility of itself, in the case that there's an atheromatous plaque on the vessel wall, the flexible cover film layer could fill up the gap formed between the inwall and the cover film layer propped by atheromatous plaque, and then could prevent the blood to flush into the aneurysm cavity. Therefore the residual blood in the villus layer will clot after some time, thus the aneurysm cavity could be sealed completely and then reaches the steady state.

The mesh structure formed by the villus performs three functions, one is to perform as a physical barrier to slow down the blood flow so as to accelerate the blood clotting, and another is to perform chemical function that PGLA can adsorb blood cells such as blood coagulation factor and blood platelet so as to accelerate the blood clotting further. Meanwhile the mesh structure performs as a fibrosis basement, which could promote fibroblast to grow into and stabilize the aneurysm cavity.

Moreover, since all the villi 431 incline toward the distal direction and the length of the villus layer 43 is not over the proximal edge of the metal mesh support layer and the cover film layer, the villi could be avoided stretching out from the edges of the endoleak preventing stent graft 40 with a villus layer, which may cause blood clotting there, may form thrombus and may further embolize the vessels under the flush of blood.

Embodiment 7

In the present embodiment 7, structures same as those of the above embodiment are given to the same numbers, and the same description is omitted.

Figure 13:
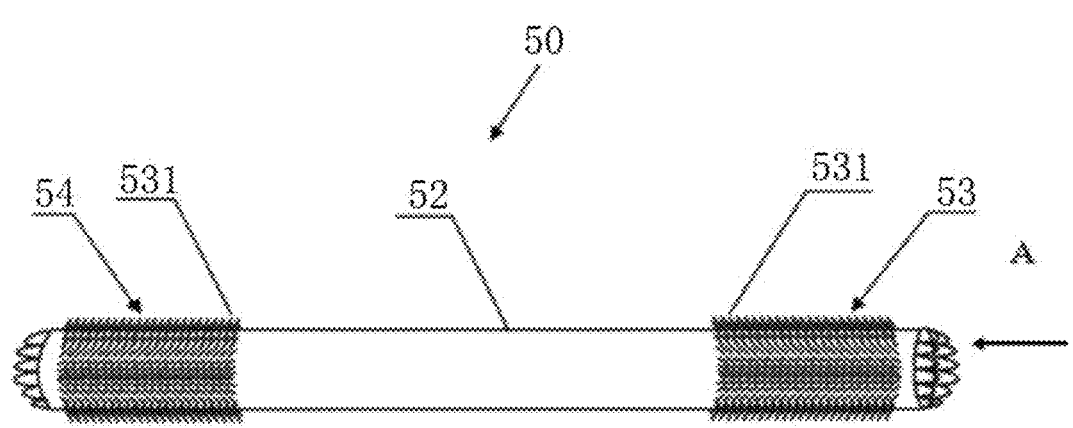
FIG. 13 is a structure illustration of an endoleak preventing stent graft with villus layers at both the proximal end and the distal end.

FIG. 13 is a structure illustration of an endoleak preventing stent graft with villus layers at both the proximal end and the distal end.

As shown in FIG. 13, the villus layers are set at both ends, namely the proximal end and the distal end. Of course, to avoid the thrombus forming in the vessels, the villi on both ends are set as inclined toward the middle part of the stent, and all villus layers are set as not covering over the edges of the proximal end and the distal end of the cover film layer and the villus layer. The advantage of setting the villus layer on both ends is to further prevent the type I endoleak occur at the distal end, even such a situation may hardly occur. Such a design could enforce the safety of the stent.

Embodiment 8

In the present embodiment 8, structures same as those of the above embodiment are given to the same numbers, and the same description is omitted.

Figure 14:
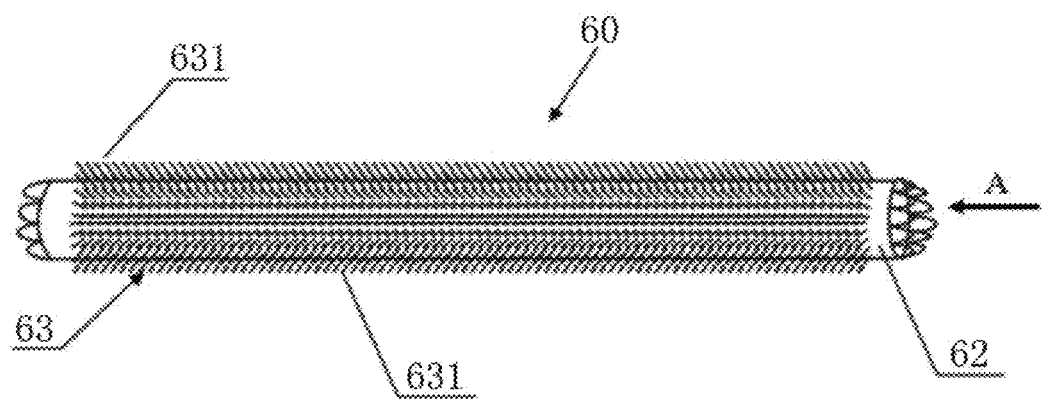
FIG. 14 is a structure illustration of the endoleak preventing stent graft system with all surface covered by a villus layer.

FIG. 14 is a structure illustration of the endoleak preventing stent graft system with all surface covered by a villus layer.

As shown in FIG. 14, the endoleak preventing stent graft with a villus layer 60 comprises a cover film layer 62 and a villus layer 63.

The metal mesh support layer locates the most inner layer, on which the cover film layer 62 covers outside. The villus layer 63 locates the outside layer of the cover film layer 62.

In the case that the villi in the villus layer of the endoleak preventing stent graft with a villus layer are spiral shape or dendriform shape, the spiral villi or the dendriform villi could form a mesh structure more firming than the linear villi, so the obstruction effect of blood could be stronger and the blood clotting could be accelerated.

In the embodiment 8, since the villus layer covers all surface of the stent, the stent could prevent type I endoleak occurring at both proximal end and distal end.

Moreover, since the villus layer is set outside the cover film layer, the stent could prevent not only type I endoleak but also type III to type V endoleak. The type III endoleak is the endoleak caused by the rupture of the cover film layer. For traditional stent, the aneurysm cavity will connect with the blood flow directly when the cover film layer ruptures. While in the present invention, since the villus layer is added, even the cover film layer ruptures, the villus layer could obstruct the aneurysm cavity and the blood flow. Since the villi in the villus layer can mesh with each other and form a porous structure, which seems like the vegetable sponge, the villus layer can slow down the blood flow when the blood flush into. So a fast flush of blood could be prevented to avoid the rupture of the aneurysm cavity. Meanwhile, since the blood flow slows down and the villus layer can adsorb blood coagulation factor and blood platelet, the residual blood in the aneurysm cavity will clot soon. So after some time the aneurysm cavity will be sealed completely by the villus layer and the clotted blood wherein. For the same reason, the type IV endoleak and type V endoleak could be prevented as well.

Moreover, the cover film layer can also cover the inner surface of the metal mesh support layer, so that the metal mesh support layer and the cover film layer connects with each other directly. Such a layer arrangement can also achieve the effects of the present invention.

Embodiment 9

In the present embodiment 9, structures same as those of the above embodiment are given to the same numbers, and the same description is omitted.

Figure 15:
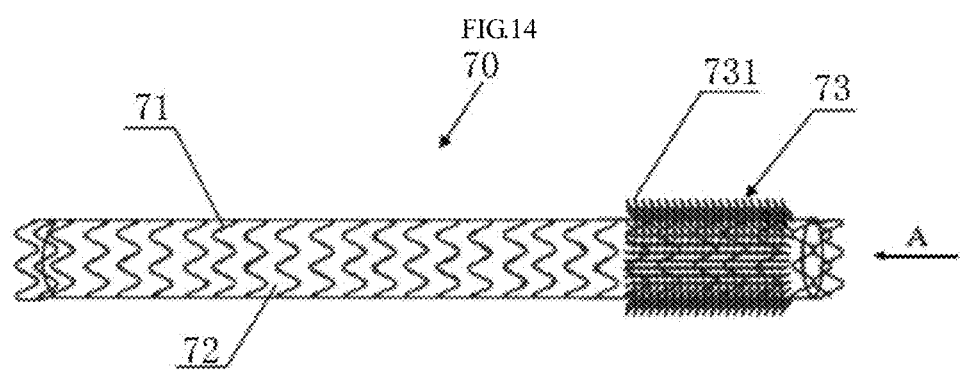
FIG. 15 is a structure illustration of the type I endoleak preventing stent graft system with the proximal end and the distal end covered by the villus layer.

FIG. 15 is a structure illustration of the type I endoleak preventing stent graft system with the proximal end and the distal end covered by the villus layer.

As shown in FIG. 15, the type I endoleak preventing stent graft 70 with the villus layer comprises a metal mesh support layer 71, a cover film layer 72 positioned inside the metal mesh support layer 71, and a villus layer 73 covering the surface of the type I endoleak preventing stent graft 70. Such a design could enforce the safety of the stent.

The villus layer 73 is formed by plural villi 731, and the villi 731 are connected onto the metal mesh support layer 71 directly. The stent with the cover film layer inside and the villus layer outside is easy to manufacture, since it is easier to connect the villi onto the metal stent than to connect the villi onto the cover film layer.

In above embodiments, the method to connect the villi onto the stent is not only planting the villi onto the cover film layer, but also planting the villi onto a leading line and then coiling the leading line as a spiral shape on the stent to make the villi distributed on the surface of the stent.

In above embodiments, the density of the villi could be controlled within the range of 500~5000 per square centimeter.

Moreover, the cover film layer can also cover the inner surface of the metal mesh support layer, so that the metal mesh support layer and the cover film layer connects with each other directly. Such a layer arrangement can also achieve the effects of the present invention.

Embodiment 10

In the present embodiment 10, structures same as those of the above embodiment are given to the same numbers, and the same description is omitted.

Figure 16:
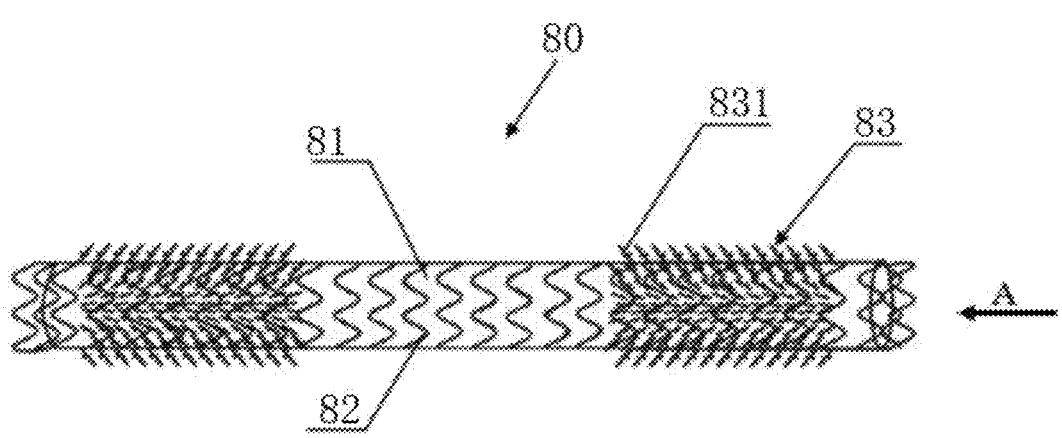
FIG. 16 is a structure illustration of the type I endoleak preventing stent graft system with all surface covered by the villus layer.

FIG. 16 is a structure illustration of the type I endoleak preventing stent graft system with all surface covered by the villus layer.

As shown in FIG. 15, the type I endoleak preventing stent graft 70 with the villus layer comprises a metal mesh support layer 81, a cover film layer 82 positioned inside the metal mesh support layer 81, and a villus layer 83 covering all the surface of the type I endoleak preventing stent graft 80.

The villus layer 83 is formed by plural villi 831, and the villi 831 are connected onto the metal mesh support layer 81 directly. The stent with the cover film layer 82 inside and the villus layer outside is easy to manufacture, since it is easier to connect the villi onto the metal stent than to connect the villi onto the cover film layer.

As shown in FIG. 16, the villus layer 83 covers both ends of the type I endoleak preventing stent graft 80 with the villus layer. The advantage of setting the villus layer on both ends is to further prevent the type I endoleak occur at the distal end. Although such a situation may hardly occur, the above design could enforce the safety of the stent.

In above embodiments, the method to connect the villi onto the stent is not only planting the villi onto the cover film layer, but also planting the villi onto a leading line and then coiling the leading line as a spiral shape on the stent to make the villi distributed on the surface of the stent.

In above embodiments, the density of the villi could be controlled within the range of 500~5000 per square centimeter.

Moreover, the cover film layer can also cover the inner surface of the metal mesh support layer, so that the metal mesh support layer and the cover film layer connects with each other directly. Such a layer arrangement can also achieve the effects of the present invention.

Embodiment 11

In the present embodiment 11, structures same as those of the above embodiment are given to the same numbers, and the same description is omitted.

Figure 17:
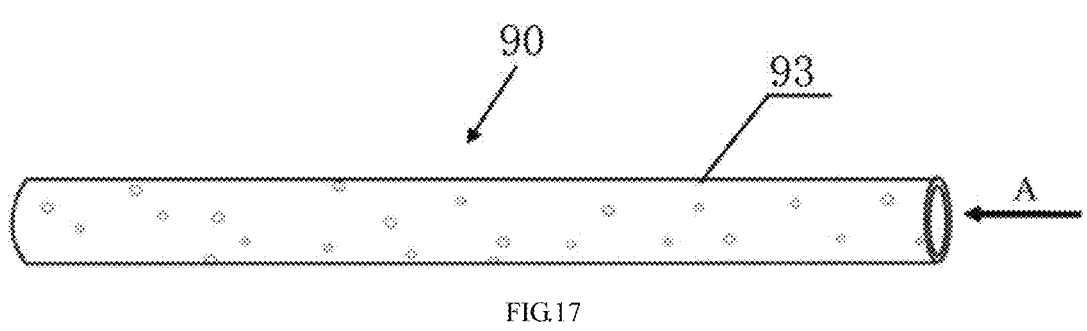
FIG. 17 is a whole structure illustration of the type I endoleak preventing stent graft system with all surface covered by the sponge layer.

FIG. 17 is a whole structure illustration of the type I endoleak preventing stent graft system with all surface covered by the sponge layer.

Figure 18:
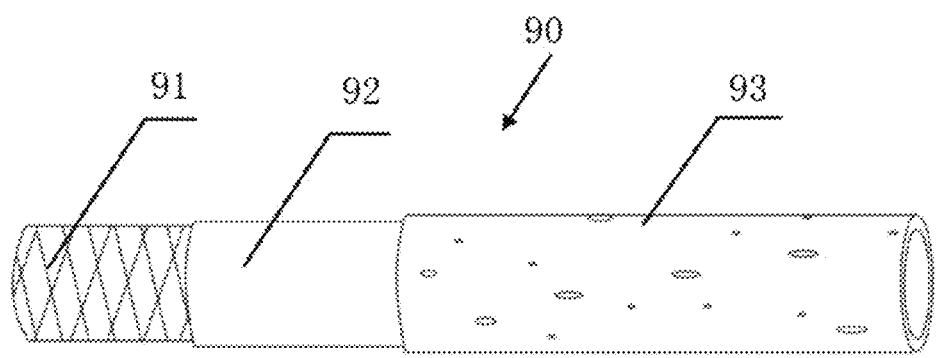
FIG. 18 is an inner structure illustration of the type I endoleak preventing stent graft system with all surface covered by the sponge layer.

FIG. 18 is an inner structure illustration of the type I endoleak preventing stent graft system with all surface covered by the sponge layer.

As shown in FIG. 17 and FIG. 18, a type I endoleak preventing stent graft 90 with a sponge structure comprises a metal mesh support layer 91, a cover film layer 92 and a sponge layer 93.

The metal mesh support layer 91 locates the most inner layer, on which the cover film layer 92 covers outside. The sponge layer 93 locates the outside layer of the cover film layer 92.

The common used material of the cover film layer 92 is Dacron, also known as ethylene glycol terephthalate. The common used material of the sponge layer is poly (lactic-glycolic acid), abbreviated as PGLA. The PGLA material can perform an adsorption function of blood coagulation factor. The sponge layer 93 is pasted onto the cover film layer.

The sponge layer covers all outside surface of the type I endoleak preventing stent graft 90 with a sponge structure, while the ends of the sponge layer do not cover over the ends of the metal mesh support layer. It is preferred that the ends of the sponge layer retract a little inward about the ends of the metal mesh support layer.

As shown in FIG. 3, FIG. 4 and FIG. 5, the type I endoleak preventing stent graft 90 with a sponge structure needs to be implanted into the blood vessel where the arterial aneurysm occurs. The atheromatous plaque 15 is on the vessel wall of the artery blood vessel 14 near by the aneurysm cavity 16. The atheromatous plaque 15 protrudes inward, and props the metal mesh support layer 91 and cover film layer 92 of the type I endoleak preventing stent graft 90 with a sponge structure, therefore a gap forms between the cover film layer 92 and the blood vessel inwall.

Since the sponge layer 93 is flexible, the sponge layer 93 can fill up the gap. Furthermore, since there's much void in the sponge layer 13, the blood flow in the gap filled with the sponge layer will slow down greatly. Meanwhile, under the effect of blood coagulation factor in the blood, the residual blood in the gap, which is filled with the sponge layer, will clot after some time and seal the gap.

There's another harmful effect of the existence of the gap. Since the gap is always flushed by the blood, the endothelial cells of the blood vessels cannot grow into the stent, which makes the endothelial cells cannot cover edges of the stent and further cannot extend to a whole with the blood vessel endothelium. However, after the type I endoleak preventing stent graft 90 with a sponge structure of the present embodiment is implanted, since the blood flow in the gap slows down, there will be enough time for the endothelial cells of the blood vessels near by the stent to grow into the inner surface of the type I endoleak preventing stent graft 90 with a sponge structure. The endothelial cells can finally cover the inner surface of the stent and become a whole with the blood vessel endothelium at both ends. Thus the stent can reach a steady state, and the blood will not flush into the aneurysm cavity any more. Furthermore, after the residual blood in the aneurysm cavity clots, the aneurysm cavity also reaches a steady state, so that the endothelial cells can grow in the aneurysm cavity and the aneurysm cavity will not rupture easily.

As shown in FIG. 17, direction A refers to the direction of the blood flow. The end near by the direction A is the proximal end, and the end away from the direction A is the distal end. The length of the sponge layer 93 is not longer than the distance between the upper edge and the bottom edge of the metal mesh support layer and the cover film layer. Such a design can avoid the sponge layer stretching out from the edges of the type I endoleak preventing stent graft 90 with a sponge structure, which may cause blood clotting there, may form thrombus and may further embolize the vessels.

The biodegradation time of PGLA could be influenced by many factors, so there're many methods to adjust the biodegradation time. One of the methods is provided hereinafter: adjust the biodegradation time by adjusting the ratio of two monomer, glycolide and lactide, in synthetic reaction. As the molar ratio of glycolide increases, the biodegradation rate increases as well. When the molar ratio is glycolide:lactide=50:50, the biodegradation time is 50~60 days. And when the molar ratio is glycolide:lactide=85:15, the biodegradation time is 150 days. The time period that the blood starts clotting and the fibroblast grows in until the fibrosis completes is within two weeks, so the biodegradation time is preferred 50~150 days for an enough time to ensure that the aneurysm cavity and the endoleak part could reach the steady state. So that the sealing of the type I endoleak will not be influenced by the short biodegradation time of PGLA.

Function and Effects of the Embodiment 11

According to the type I endoleak preventing stent graft system with a sponge structure provided in the embodiment, since the sponge layer is set outside the cover film layer and the sponge layer can fill up the gap formed between the cover film layer and the inwall under the effect of the flexibility of itself, in the case that there's an atheromatous plaque on the vessel wall, the flexible cover film layer could fill up the gap formed between the inwall and the cover film layer propped by atheromatous plaque, and then could prevent the blood to flush into the aneurysm cavity. Therefore the residual blood in the sponge layer will clot after some time, thus the aneurysm cavity could be sealed completely and then reaches the steady state.

The mesh structure formed by the sponge layer performs three functions, one is to perform as a physical barrier to slow down the blood flow so as to accelerate the blood clotting, and another is to perform chemical function that PGLA can adsorb blood cells such as blood coagulation factor and blood platelet so as to accelerate the blood clotting further. Meanwhile the mesh structure performs as a fibrosis basement, which could promote fibroblast to grow into and stabilize the aneurysm cavity.

Moreover, since the length of the sponge layer is not longer than the distance between the upper edge and the bottom edge of the metal mesh support layer and the cover film layer, it could be avoid that the sponge layer stretches out from the edges of the type I endoleak preventing stent graft 90 with a sponge structure, which may cause blood clotting there, may form thrombus and may further embolize the vessels.

The implanting method of the type I endoleak preventing stent graft 90 with a sponge structure:

Set the type I endoleak preventing stent graft 90 with a sponge structure onto a stents conveyor, and then convey it to the vasculopathy position by the stents conveyor. Release the self-expanding stent gradually by a release device to make the type I endoleak preventing stent graft 90 with a sponge structure seal the blood flow in the aneurysm cavity, and then pull the conveyor out. So that the stent can be placed at the vasculopathy position to achieve the purpose of sealing the aneurysm cavity.

During the operation, a digital subtraction angiography (DSA) can be used for monitoring the whole process inside human body that the conveyor enters the aorta from the arteriole and finally reaches the aneurysm cavity.

Embodiment 12

In the present embodiment 12, structures same as those of the above embodiment are given to the same numbers, and the same description is omitted.

Figure 19:
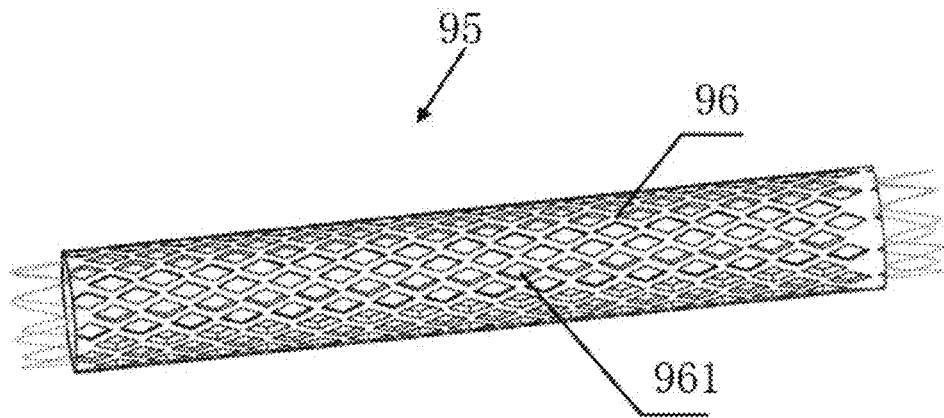
FIG. 19 is a structure illustration of the type I endoleak preventing stent graft system with a rhombus grid sponge layer.

FIG. 19 is a structure illustration of the type I endoleak preventing stent graft system with a rhombus grid sponge layer.

As shown in FIG. 19, the sponge layer of the type I endoleak preventing stent graft 95 with a sponge layer comprises plural even-distributed rhombus grids 96, and the rhombus grid 96 comprises a rhombus groove 961.

On one hand, the rhombus groove 961 can save material of the sponge, on the other hand, the rhombus groove 961 can provide a space for fitting the atheromatous plaque after being implanted.

Meanwhile, since the surface of the sponge is not plane, the only parts that the atheromatous plaque needs to prop are the embossing edges of the rhombus grids 96, so the force performs on the atheromatous plaque is quite small. On the other side, compared with the full filled sponge in embodiment 6, the stent in the present embodiment performs a smaller force on the atheromatous plaque and the blood vessel inwall, and performs less stimulation on the vessels.

Moreover, since the sponge layer is set outside the cover film layer and the sponge layer provides a mesh structure there, the stent could prevent not only type I endoleak but also type III to type V endoleak. The type III endoleak is the endoleak caused by the rupture of the cover film layer. For traditional stent, the aneurysm cavity will connect with the blood flow directly when the cover film layer ruptures. While in the present invention, since the sponge layer is added, even the cover film layer ruptures, the sponge layer could obstruct the aneurysm cavity and the blood flow. Since the sponge layer provides the mesh structure there, the sponge layer can slow down the blood flow when the blood flush into. So the fast flush of blood could be prevented to avoid the rupture of the aneurysm cavity. Meanwhile, since the blood flow slows down and the sponge layer can adsorb blood coagulation factor and blood platelet, the residual blood in the aneurysm cavity will clot soon. So after some time the aneurysm cavity will be sealed completely by the sponge layer and the clotted blood wherein. For the same reason, the type IV endoleak and type V endoleak could be prevented as well.

Moreover, the cover film layer can also cover the inner surface of the metal mesh support layer, so that the metal mesh support layer and the cover film layer connects with each other directly. Such a layer arrangement can also achieve the effects of the present invention.

Embodiment 13

In the present embodiment 13, structures same as those of the above embodiment are given to the same numbers, and the same description is omitted.

The endoleak preventing stent graft with the sponge layer in the present invention comprises a metal mesh support layer fit for the artery blood vessel; cover film layer positioned on said metal mesh support layer; flexible mesh layer positioned outside of the stent. Such a design could enforce the safety of the stent.

Said cover film layer positioned on said metal mesh support layer refers to a cover film layer covering the whole external surface of the metal mesh support layer.

Obviously, the flexible mesh layer can also be formed by prisms with other polyhedral shapes, such as hexahedron and tetrahedron. The preferred shape is elongated triangular bipyramid, a kind of enneahedron, used in the present embodiment.

Obviously, it is preferred that the long axis of the basic form unit is perpendicular to the central axis of the stent, while the two directions can be set as other angles. Of cause the closer the angle is to the vertical, the better the effect.

What is claimed is:

1. An endoleak preventing stent graft system, comprising:
   a metal mesh support layer fit for the shape of said artery blood vessel;
   a cover film layer covering the surface of said metal mesh support layer; and
   a flexible mesh layer positioned outside said cover film layer, said flexible mesh layer fills up the gap formed between said cover film layer and the inwall of said artery blood vessel under the effect of the flexibility of itself;
   wherein said flexible mesh layer is formed by plural prisms with polyhedral shape;
   wherein a part of said polyhedrons or all of said polyhedrons are hollowed out.

2. The endoleak preventing stent graft system according to claim 1,
   wherein said polyhedron is elongated triangular bipyramid.

* * * * *